(12) United States Patent
Kennedy, II

(10) Patent No.: US 7,637,873 B2
(45) Date of Patent: Dec. 29, 2009

(54) WIRE GUIDES HAVING NOVEL OUTER SURFACE AREAS AND RESERVOIRS FOR ENHANCING HYDROPHILIC PROPERTIES AND DELIVERING THERAPEUTIC AGENTS

(75) Inventor: Kenneth C. Kennedy, II, Clemmons, NC (US)

(73) Assignee: Winston-Cook Medical Inc., Winston-Salem, NC (US)

( * ) Notice: Subject to any disclaimer, the term of this patent is extended or adjusted under 35 U.S.C. 154(b) by 309 days.

(21) Appl. No.: 11/377,712

(22) Filed: Mar. 15, 2006

(65) Prior Publication Data

US 2006/0211952 A1   Sep. 21, 2006

Related U.S. Application Data

(60) Provisional application No. 60/663,034, filed on Mar. 18, 2005.

(51) Int. Cl.
*A61M 25/00* (2006.01)
*A61M 31/00* (2006.01)

(52) U.S. Cl. .................. 600/585; 604/500; 604/506

(58) Field of Classification Search .................. 600/434, 600/585; 604/523, 890.1, 891.1, 892.1; 424/422
See application file for complete search history.

(56) References Cited

U.S. PATENT DOCUMENTS

| | | | | |
|---|---|---|---|---|
| 4,717,379 A | * | 1/1988 | Ekholmer | 604/43 |
| 4,925,445 A | * | 5/1990 | Sakamoto et al. | 604/528 |
| 5,112,305 A | * | 5/1992 | Barath et al. | 604/103.01 |
| 5,423,745 A | * | 6/1995 | Todd et al. | 604/500 |
| 5,596,996 A | * | 1/1997 | Johanson et al. | 600/585 |
| 5,800,407 A | * | 9/1998 | Eldor | 604/264 |

(Continued)

FOREIGN PATENT DOCUMENTS

WO   WO 92/11890   7/1992

(Continued)

OTHER PUBLICATIONS

Written Opinion, dated Mar. 8, 2007, for International Application No. PCT/US2006/009171.

(Continued)

*Primary Examiner*—Max Hindenburg
*Assistant Examiner*—Adam J Eiseman
(74) *Attorney, Agent, or Firm*—Brinks Hofer Gilson & Lione

(57) ABSTRACT

Wire guides and methods of using an elongate wire guide with a first end portion and a flexible second end portion having an increased surface area is provided. The second end portion comprises a nominal outer circumference disposed about a longitudinal axis and having a first outer surface including the nominal outer circumference and defining a first surface area. Protuberances, indentations, peaks, and/or valleys are disposed substantially circumferentially about the nominal outer circumference and defining an effective perimeter greater than the nominal outer circumference and having a second outer surface defining a second surface area greater than the first surface area. Hydrophilic materials and therapeutic agents may be disposed partially on the second end portion and a coating, and a membrane may be disposed about second end portion and coating to form reservoirs or lumens for delivering hydrophilic materials and delivering therapeutic agents.

17 Claims, 11 Drawing Sheets

U.S. PATENT DOCUMENTS

| | | | | |
|---|---|---|---|---|
| 5,824,049 | A | * | 10/1998 | Ragheb et al. ............. 623/1.44 |
| 5,891,101 | A | * | 4/1999 | Wilcox et al. ............... 604/175 |
| 6,146,358 | A | * | 11/2000 | Rowe .................... 604/103.02 |
| 6,179,816 | B1 | * | 1/2001 | Mottola et al. .............. 604/264 |
| 6,197,013 | B1 | * | 3/2001 | Reed et al. ................. 604/509 |
| 6,296,616 | B1 | | 10/2001 | McMahon |
| 6,635,027 | B1 | * | 10/2003 | Cragg et al. ................. 604/22 |
| 7,070,592 | B2 | * | 7/2006 | Santini et al. ............ 604/891.1 |
| 2002/0087100 | A1 | * | 7/2002 | Onuki et al. ................ 600/585 |
| 2004/0073284 | A1 | * | 4/2004 | Bates et al. ................ 623/1.11 |
| 2004/0230136 | A1 | * | 11/2004 | Corrigan, Jr. ............... 600/585 |
| 2006/0135941 | A1 | * | 6/2006 | Porto et al. ................. 604/500 |

FOREIGN PATENT DOCUMENTS

| | | |
|---|---|---|
| WO | WO 94/19039 | 9/1994 |

OTHER PUBLICATIONS

Search Report and Written Opinion, dated Jul. 11, 2006, for International Application No. PCT/US2006/009171.

* cited by examiner

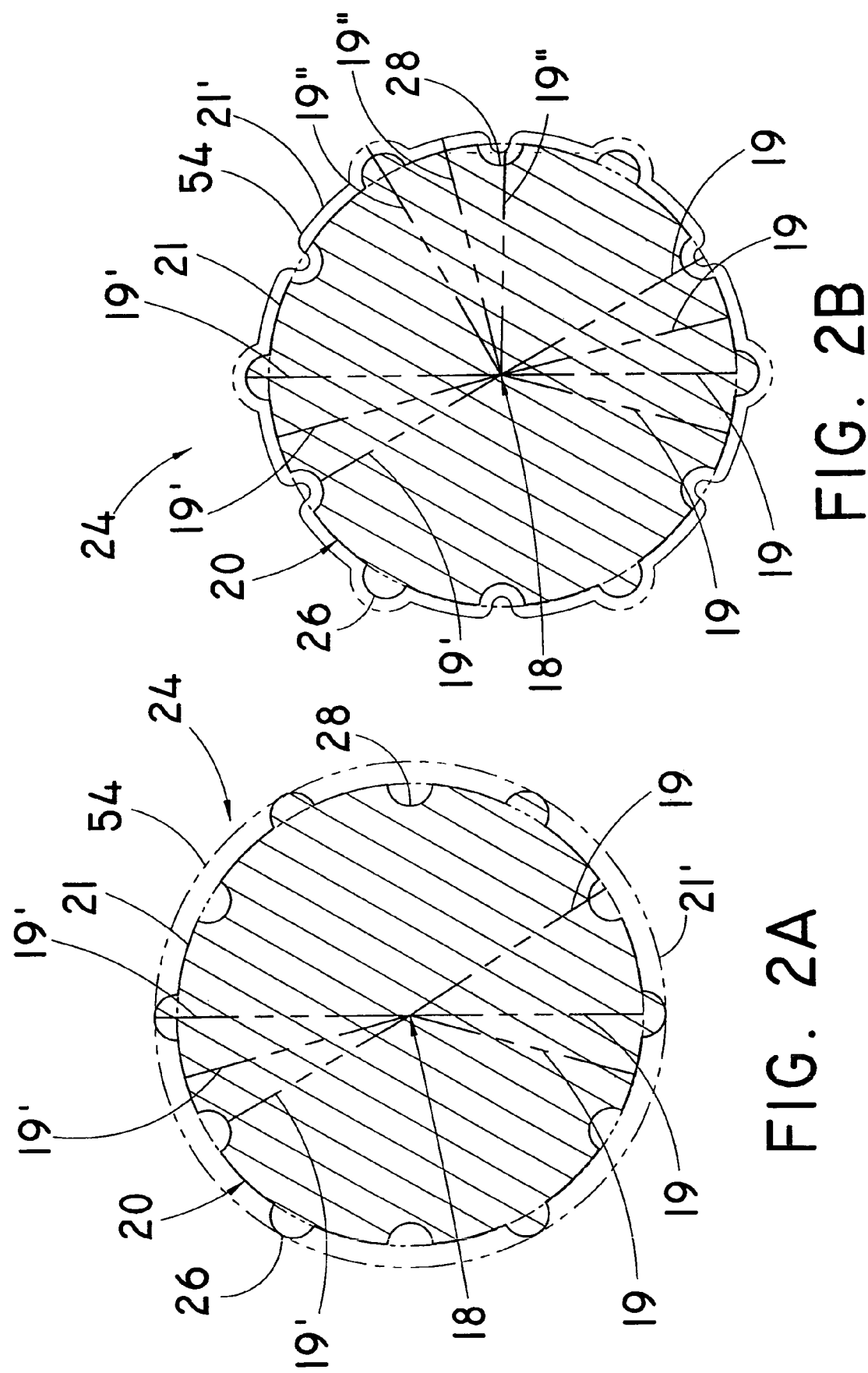

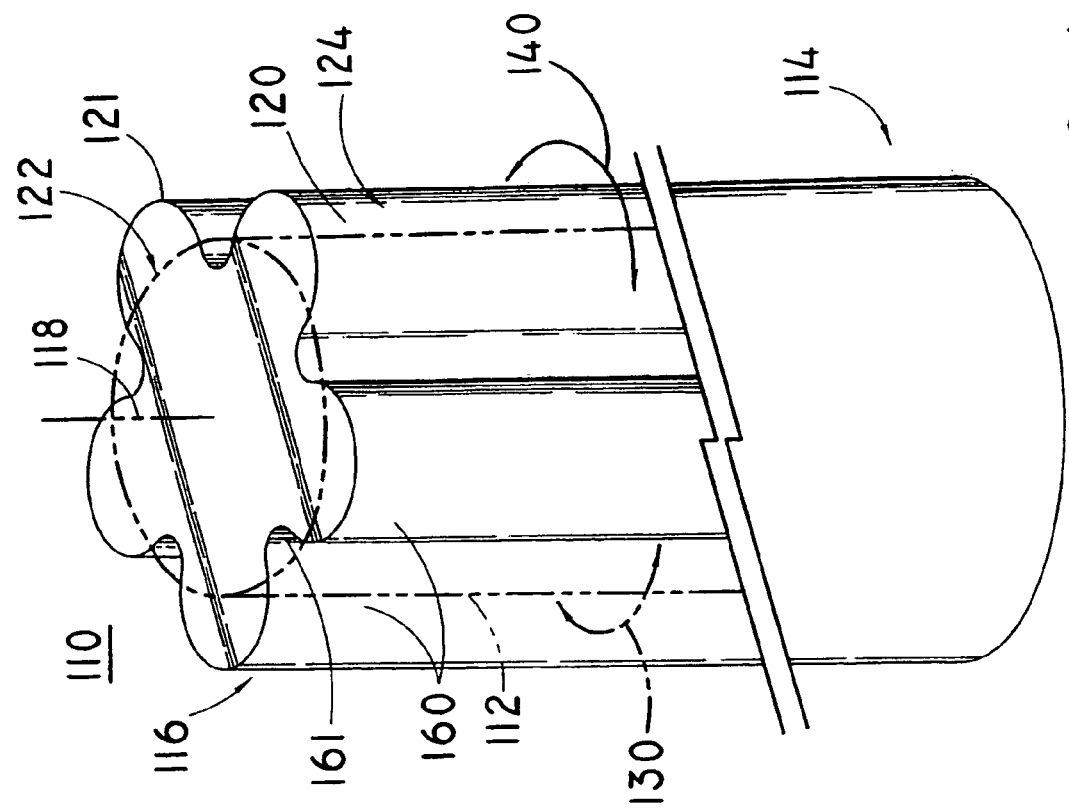
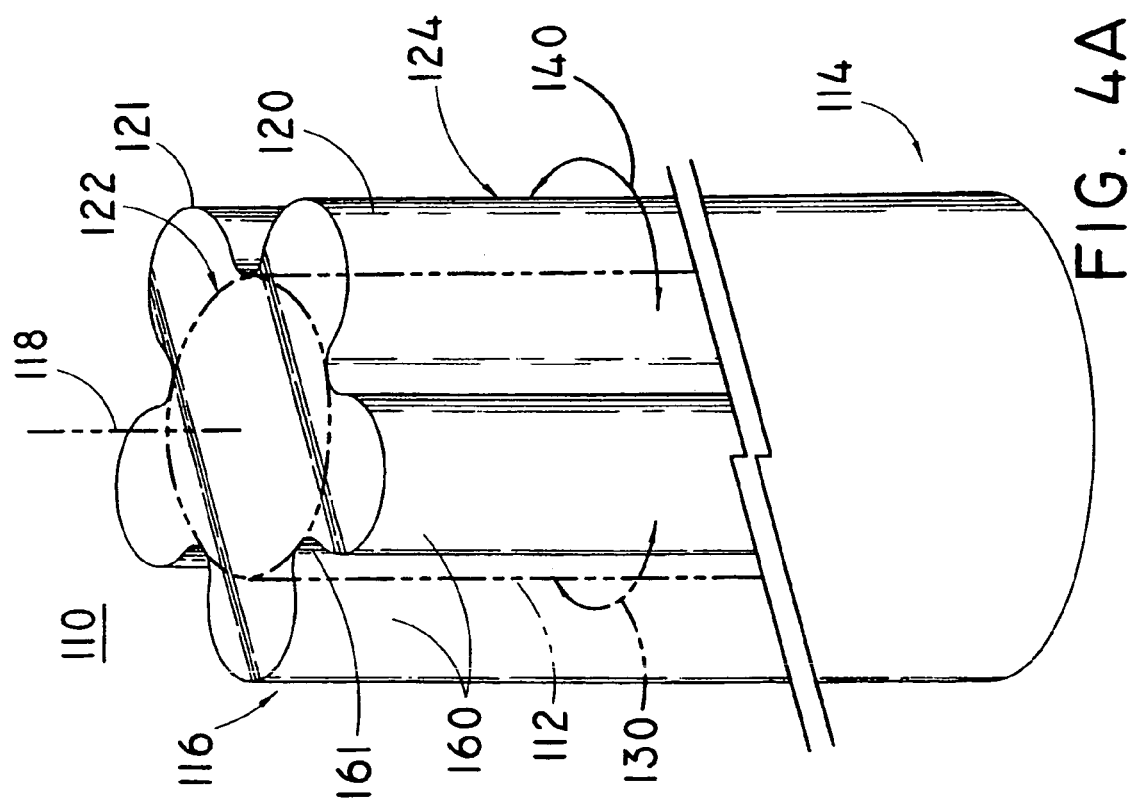

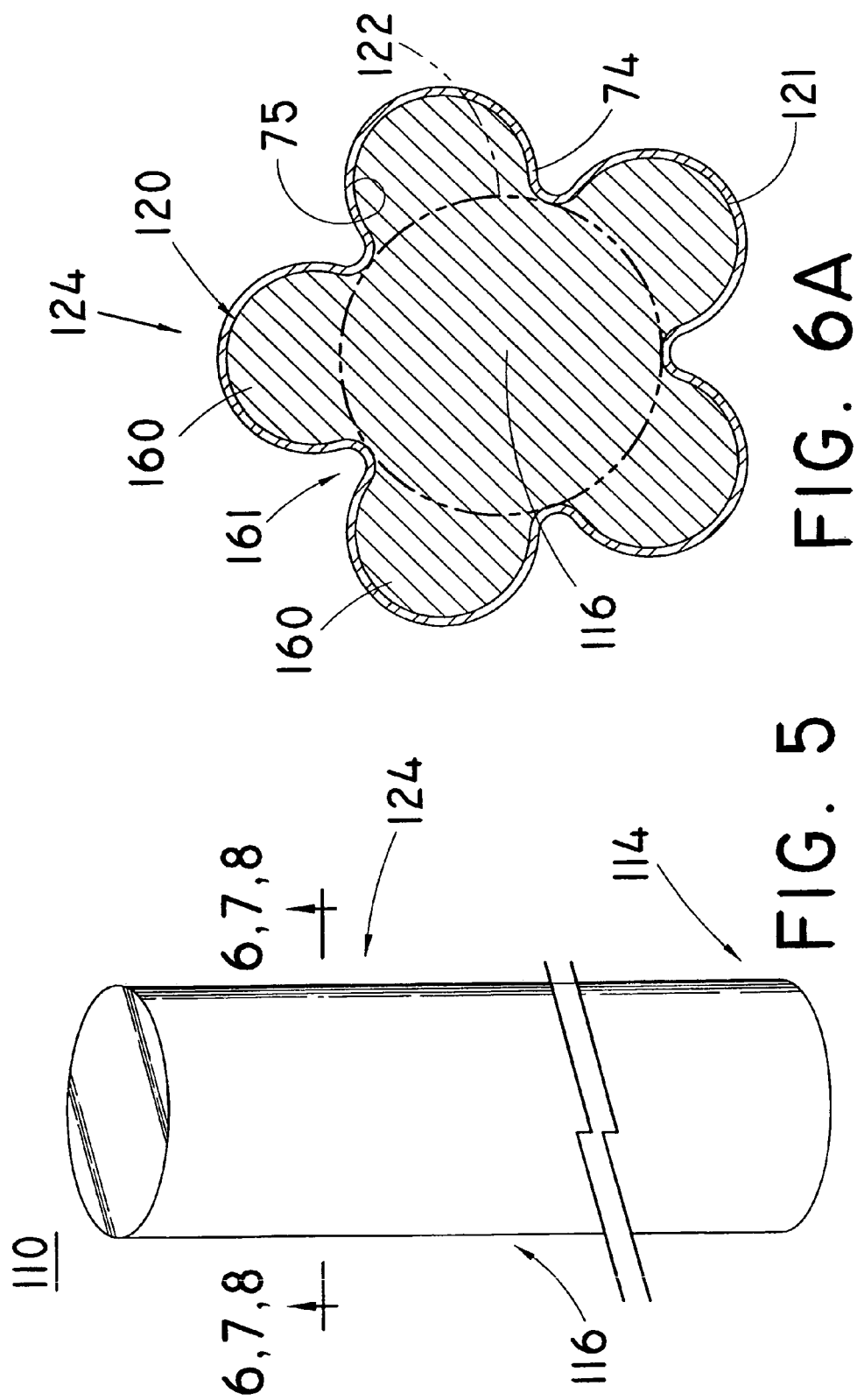

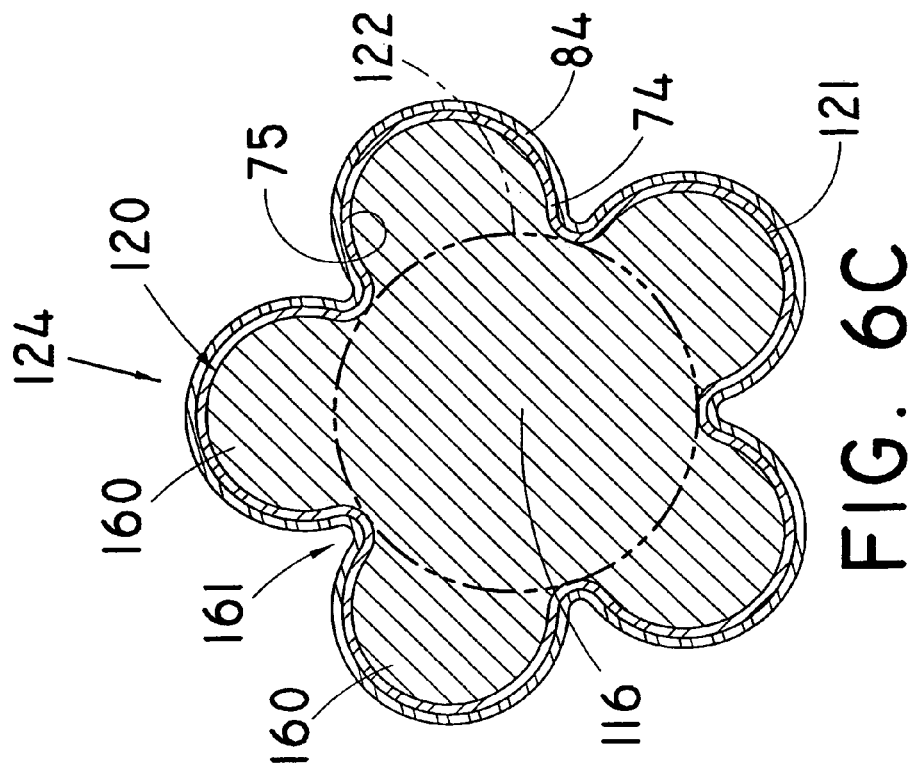
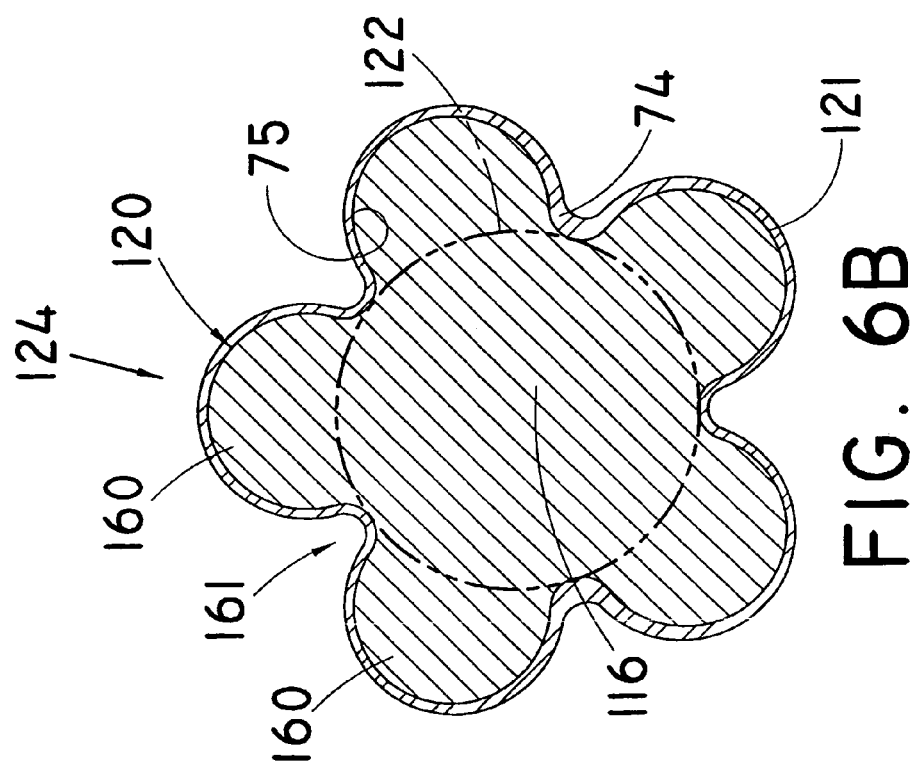

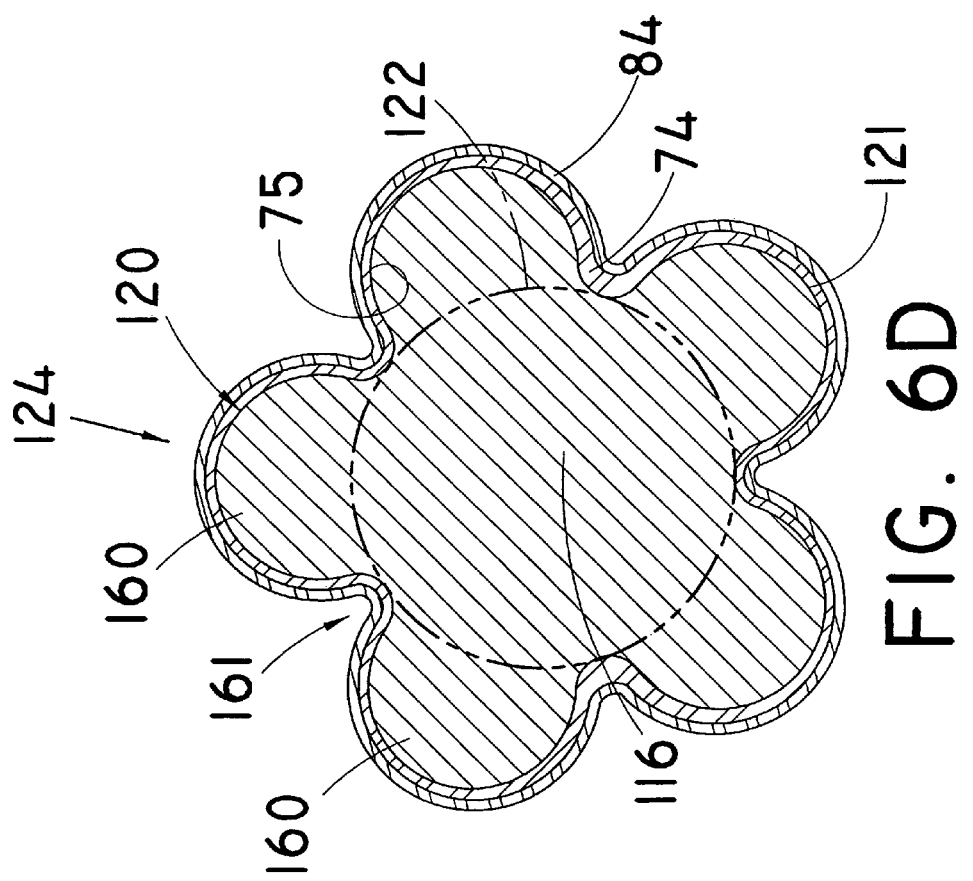

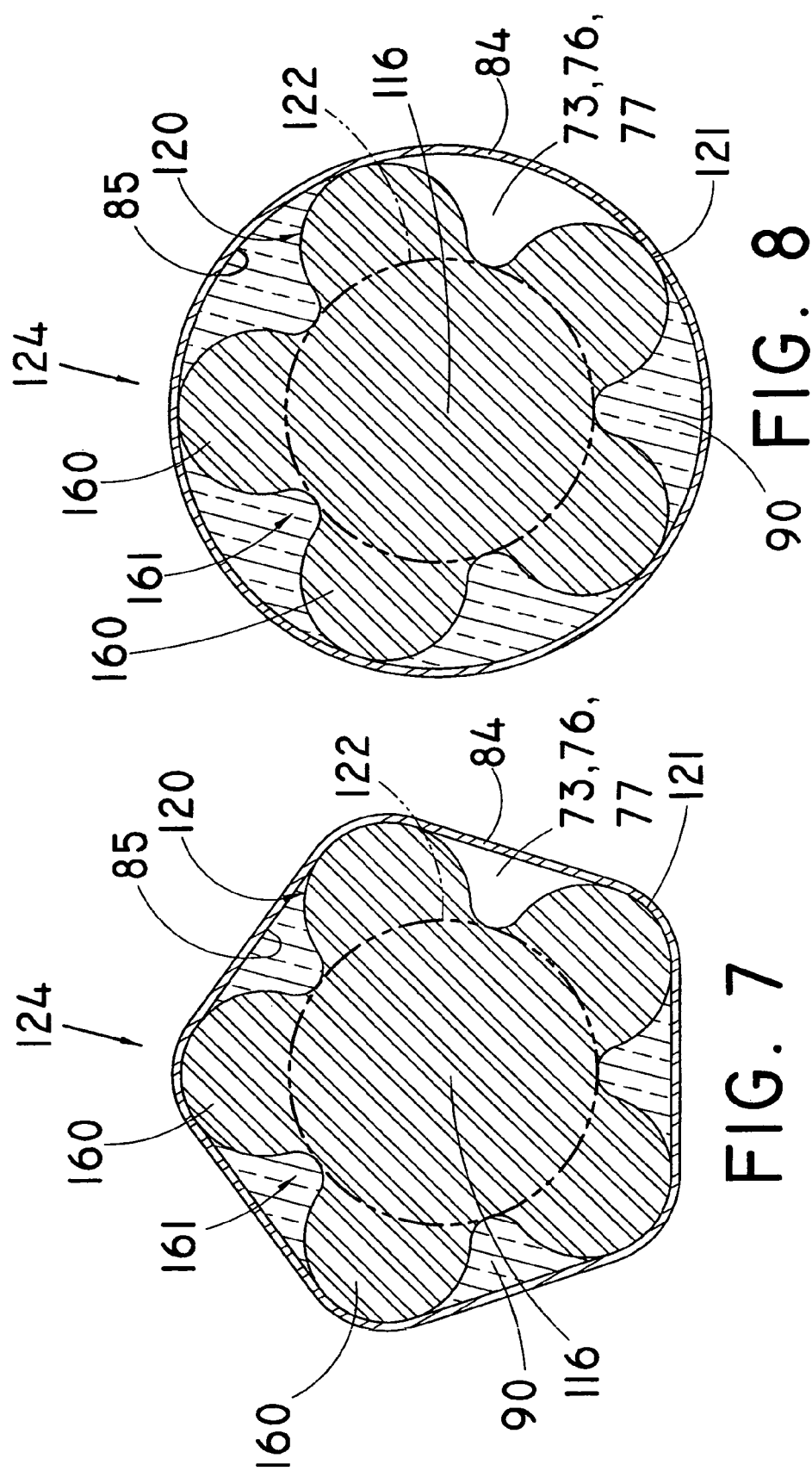

WIRE GUIDES HAVING NOVEL OUTER SURFACE AREAS AND RESERVOIRS FOR ENHANCING HYDROPHILIC PROPERTIES AND DELIVERING THERAPEUTIC AGENTS

RELATED APPLICATIONS

The present patent document claims the benefit of the filing date under 35 U.S.C. §119(e) of Provisional U.S. Patent Application Ser. No. 60/663,034, filed Mar. 18, 2005, which is hereby incorporated by reference in its entirety.

FIELD OF THE INVENTION

The present invention relates to wire guides for use with endoscopes or percutaneously within a vascular system, the biliary system, the pancreas, and the like, and methods of using those devices. The wire guides have increased surface area for enhancing hydrophilic properties and delivering therapeutic agents.

BACKGROUND OF THE INVENTION

By way of background, a physician or other healthcare professional (collectively, "physician") often uses wire guides in a variety of medical procedures. For instance, the physician commonly uses wire guides as one preferred instrument for the placement of another elongate medical device, such as a catheter or stent delivery system, into a vessel passageway. The term "passageway" includes any lumen, chamber, channel, opening, bore, orifice, flow passage, duct, or cavity for the conveyance, regulation, flow, or movement of bodily fluids and/or gases of an animal. As examples of the various passageways into which wire guides may be utilized, physicians frequently use wire guides in medical procedures that involve placing a wire guide in the passageways of an aorta, artery, bile duct, blood vessel, brachial, bronchiole, capillary, esophagus, fallopian tube, gall bladder, gastrointestinal tract, heart, intestine, liver, pancreas, stomach, trachea, ureter, urethra, vein, and other locations in a body (collectively, "vessel") to name a few. Similarly, physicians may place wire guides through a working channel of an endoscope (or an accessory channel used with an endoscope) in endoscopic medical procedures such as those described below.

As a backdrop to an understanding of a conventional endoscope, these medical instruments generally include a light source and image sensor for visualizing the interior of an internal region of a body. In the field of endoscopy, physicians use a variety of different endoscopes in a wide range of applications. These different types of endoscopes include, by way of example, the following: arthroscope, bronchoscope, choledochoscope, colonoscope, cytoscope, duodenoscope, gastroscope, laparascope, neproscope, sigmoidoscope, uterscope, or any external accessory channel device used with any of the foregoing (collectively, "endoscope").

In exemplary endoscopic uses of wire guides, a physician introduces at least a portion of the wire guide through a working channel of an endoscope or an accessory channel external to an endoscope. As another alternative, the physician inserts at least a portion of the wire guide through a catheter lumen, which catheter the physician has already inserted, or intends to insert, into the endoscope working channel or accessory channel.

In exemplary percutaneous uses of wire guides, a physician inserts the wire guide into the vessel passageway by a variety of suitable methods. In one instance, the physician may create an incision in a region of the patient's body, position a cannula at the incision, and then insert the wire guide through the cannula. Alternatively, the physician may insert a needle—containing the wire guide—into a vessel such as an artery, bile duct, brachial vein, cephalic vein, pancreatic ducts, or other vessel as described above, and then introduce the wire guide through the needle into the vessel passageway. In a subsequent step, the needle is withdrawn over the wire guide.

In these various wire guide uses, physicians and others normally evaluate and select wire guides with respect to several performance criteria including: column strength, flexibility, and torsional stiffness. As one criterion, the column strength of a wire guide must be sufficient to allow the wire guide to be pushed through the endoscope or accessory channel, the catheter, or the patient's vessel passageway without kinking or prolapsing. In another criterion, the flexibility of a wire guide must be sufficient to navigate a tortuous vessel passageway and to avoid damaging the vessel through which the physician advances the wire guide. A third performance criterion of a wire guide relates to its torque-ability or steerability. This third criterion denotes the extent to which a wire guide possesses the capability of transferring a torque in a one-to-one relationship from the proximal end to the distal end of the wire guide without excess twisting that may result in a whipping effect caused by torque build-up in the wire guide.

Depending upon the materials used to construct the wire guide, the above three characteristics are often interconnected or interrelated to one extent or another. In other words, often with some wire guides these performance criteria compete in that an increase in one criterion compromises another criterion. For example, increased column strength may mean a decrease in flexibility, and vice versa. Indeed, when constructing wire guides, the limits of the metals used for making conventional wire guides often necessitate sacrificing one performance characteristic in favor of another. By way of example only, increasing the torque-ability of a given wire guide may often decrease the flexibility and/or pushability in a wire guide of conventional composition or shape.

In order to negotiate a tortuous path of a vessel passageway or to avoid passageway obstacles during insertion as described above, conventional wire guides have a proximal end that is sometimes held by or otherwise secured by a physician, and a distal end to be located at or near the target site. As is conventional, "distal" means away from the physician or operator when the device is inserted into a patient, while "proximal" means closest to or toward the physician or operator when the device is inserted into a patient.

The shape of a typical wire guide is normally generally cylindrical with a substantially circular cross section to mimic the configuration of the vessel passageway or the channel of an endoscope or accessory device. Some conventional wire guides occasionally have stainless steel or nitinol wire cores wrapped in a longitudinal Teflon coated coil, thereby increasing the diameter and stiffness of the wire guide and making the wire guides hydrophobic and resistant to coating with a hydrophilic material and/or therapeutic agent. By comparison, conventional non-coiled wire guides typically have a smooth outer surface and a tapered distal end with a reduced diameter measured in thousandths of an inch diameter, thereby increasing the flexibility of the wire guide but decreasing the outer surface area at the distal end of the wire guide. Improvements are possible to achieve flexibility while also increasing surface area to provide a wire guide with more functionality.

Therefore, improved wire guides would be desirable. As taught herein, these wire guides comprise novel approaches to tailoring wire guides to have increased outer surface areas and/or reservoirs for enhancing hydrophilic properties and for delivering therapeutic agents.

SUMMARY OF THE INVENTION

Wire guides for use with endoscopes or percutaneously, such as within the vascular system, the biliary, the pancreas, and the like are provided. In one embodiment, an elongate shaft has a first end portion and a flexible second end portion. A non-coiled portion of the flexible second end portion has a nominal outer circumference. A plurality of textures are disposed circumferentially about the nominal outer circumference for increasing the overall surface area of that non-coiled portion having textures.

In another embodiment, an elongate shaft has a first end portion and a flexible second end portion. A non-coiled portion of the flexible second end portion has a nominal outer circumference. A plurality of peaks and valleys are disposed circumferentially about the nominal outer circumference for increasing the overall surface area.

In a further embodiment, an elongate wire guide comprises a first end portion and a flexible second end portion, a non-coiled portion of the flexible second end portion has a nominal outer circumference, and a plurality of peaks and valleys, whereby adjacent peaks define the valley therebetween, are disposed circumferentially about the nominal outer circumference. A membrane is disposed about at least one valley for forming a reservoir extending along the valley and to a space exterior to the wire guide. The reservoir may contain a therapeutic agent.

Methods of providing a wire guide for intracorporeal procedures are also provided. In one embodiment, a method according to the invention includes providing a wire guide having a first end and a flexible second end comprising a nominal outer circumference and textures disposed circumferentially about the nominal outer circumference, wherein the textures increasing the outer surface area. A tubular member, such as a cannula, a needle, an endoscope working channel, or an accessory channel used with an endoscope, is provided. The tubular member has openings at first and second ends defining a lumen therebetween. The tubular member second end is placed into a patient endoscopically or percutaneously. The wire guide second end is advanced through the tubular member first end opening, the lumen, and the second end opening.

BRIEF DESCRIPTION OF THE DRAWINGS

FIG. 2A is a cross sectional view of FIG. 2 taken along the line 2A-2A.

FIG. 2B is a cross sectional view of FIG. 2 taken along the line 2B-2B.

FIGS. 4A and 4B are perspective views, broken away, of wire guide devices according to alternative embodiments of the invention.

FIG. 5 is a schematic view, broken away, of a wire guide device according to an embodiment of the invention.

FIG. 6A is a cross sectional view of FIG. 5 taken along the line 6-6 according to an embodiment of the invention having a coat.

FIG. 6B is an alterative embodiment of FIG. 6A having a coat with one or more thickened regions.

FIG. 6C is an alternative embodiment of FIG. 6A having an outer membrane.

FIG. 6D is an alternative embodiment of FIG. 6B having an outer membrane.

FIG. 7 is a cross sectional view of FIG. 5 taken along the line 7-7 according to an alternate embodiment of the invention.

FIG. 8 is a cross sectional view of FIG. 5 taken along the line 8-8 according to another embodiment of the invention.

DETAILED DESCRIPTION OF THE PREFERRED EMBODIMENTS

Although not limited in its scope or applicability, the present invention relates generally to a wire guide device used percutaneously (such as within the vascular system, the biliary system, the pancreas, and the like), endoscopically, or with, for instance, catheters and the like, and methods of using those devices. More particularly and by way of illustration and not by way of limitation, the present invention relates to wire guides having increased outer surface areas and/or reservoirs, wherein the increased outer surface areas and/or reservoirs of the wire guides are adapted for enhancing hydrophilic properties and/or delivering therapeutic agents.

For the purpose of promoting an understanding of the principles of the present invention, the following provides a detailed description of embodiments of the invention as illustrated by the drawings as well as the language used herein to describe the aspects of the invention. The description is not intended to limit the invention in any manner, but rather serves to enable those skilled in the art to make and use the invention. As used herein, the terms comprise(s), include(s), having, has, with, contain(s) and variants thereof are intended to be open ended transitional phrases, terms, or words that do not preclude the possibility of additional steps or structure.

Given the configuration of vessels and vessel passageways to be navigated, conventional wire guides are cylindrical. A cylindrical shape may be better tolerated by the patient to minimize pain and discomfort, or to navigate the patient's vessel passageway, a catheter, an endoscope working channel, or the accessory channel used with an endoscope. Furthermore, in order to increase flexibility and thereby reduce the risk of damaging a vessel passageway, the conventional wire guide usually tapers distally to smaller cross sections having less surface area than might be desired. In order to increase the surface area, the wire guide may be made bigger by increasing the diameter of the guide wire cross sections, but this would be less optimal in vessels having small vessel passageways. Also, the larger wire guide may be uncomfortable for the patient. According to embodiments of the invention, the wire guide would have an increased surface area without sacrificing comfort, tolerance, or safety to the patient.

Figure 1:
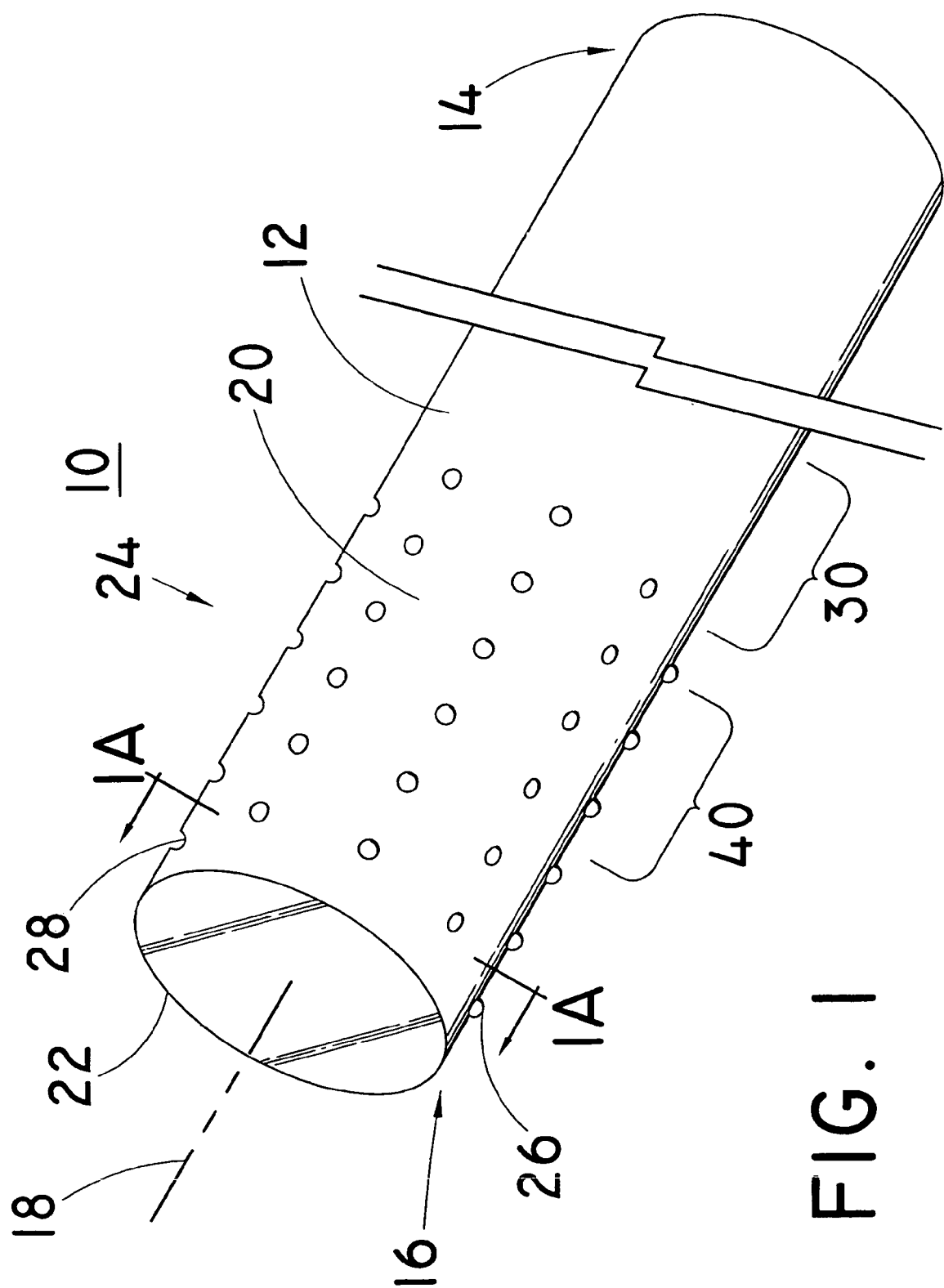
FIG. 1 is a perspective side view, broken away, of a wire guide device according to one embodiment of the invention.
Figure 1A:
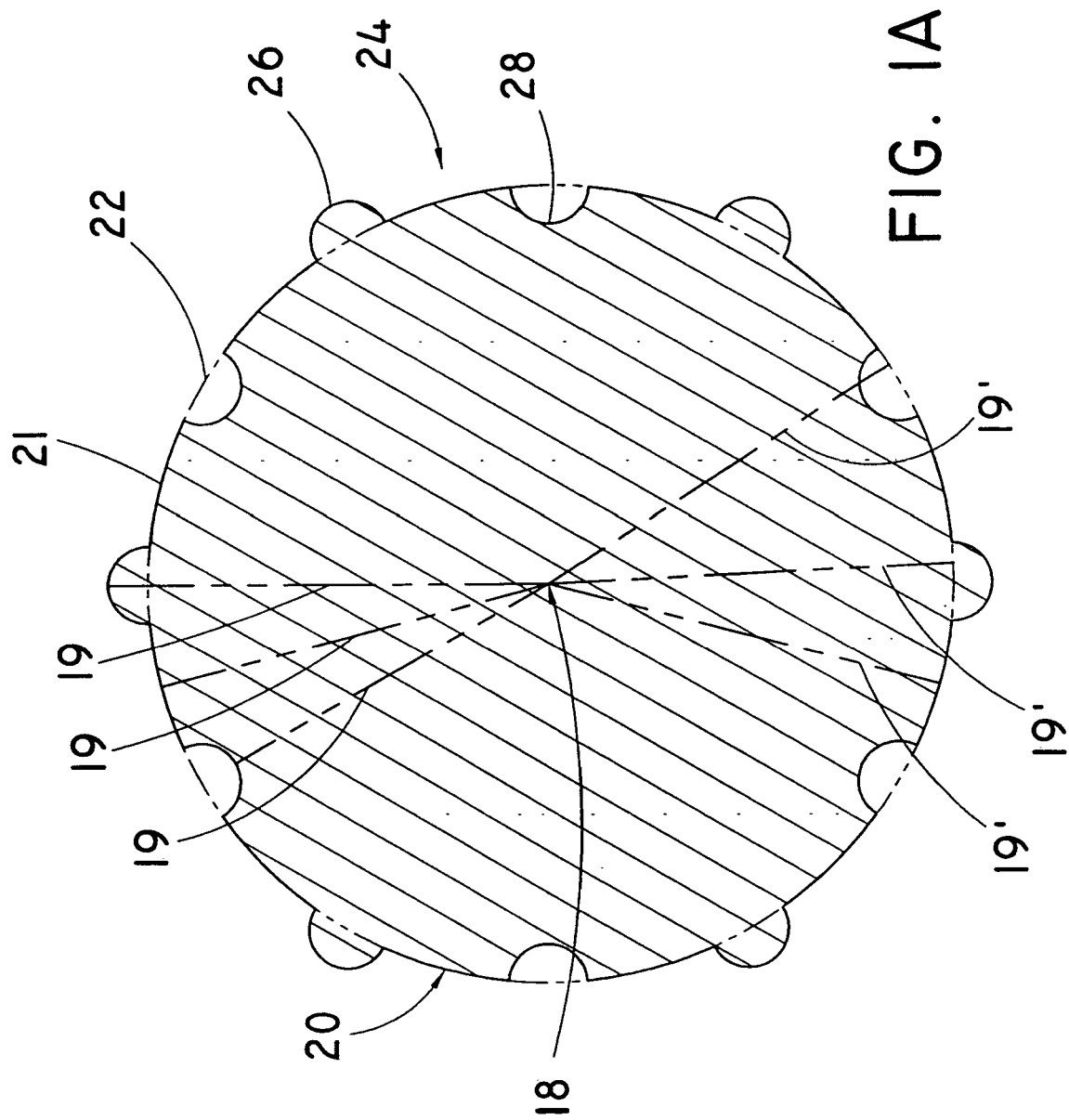
FIG. 1A is a cross sectional view of FIG. 1 taken along the line 1A-1A.

FIG. 1 and FIG. 1A (taken along the line 1A-1A of FIG. 1) show a wire guide device having an elongate shaft 10 according to one embodiment of the invention for increasing the surface area, and for enhancing hydrophilic properties and/or delivering therapeutic agents. This embodiment comprises a first end portion 14 and a flexible second end portion 16. The second end portion 16 extends distally from the first end portion 14. In describing embodiments of the invention, an elongate shaft 10 could be any shaft-like, rounded, oblong, circular, rectangular, square, tube-like, cylindrical, or generally rod-like structure utilized as a wire guide for percutaneous, biliary, pancreatic, catheter, accessory channels, or endoscopic uses. In one embodiment, the elongate shaft 10 is a wire guide. In another embodiment, a wire guide comprises an elongate shaft 10 having a first end portion 14 and a flexible second end portion 16, as described below. As is conventional for wire guides, the elongate shaft 10 typically utilizes work hardened surgical stainless steel or a shape memory alloy such as nickel-titanium alloy ("nitinol"), copper-zinc-aluminum, iron-manganese-silicon, gold-cadmium, copper-aluminum, and copper-aluminum-nickel, although any conventional material for wire guides may be used.

The term "elongate," in describing any of the embodiments of the wire guide device having an elongate shaft 10, means greater than about 50 centimeters ("cm"). The overall length of the guide wire may vary, however, and in one embodiment the elongate shaft 10 has a length of between about 50 cm and about 600 cm, although the elongate shaft 10 may be shorter or longer, as desired. In another embodiment, the elongate shaft 10 may be in the range of about 185 cm to about 480 cm. The diameter of the elongate shaft 10 may be, by way of example only and not by way of limitation, between about 0.25 millimeters ("mm") and about 1.25 mm, and the diameter may generally taper in the distal direction. Furthermore, the elongate shaft 10 diameter may vary and be greater or less than this range at certain positions along the length of the elongate shaft 10. For instance, the diameter of the elongate shaft 10 may be greater than 1.25 mm at the first end portion 14 and less than 0.25 mm at the second end portion 16 or along a portion of the second end portion 16.

Moreover, the length of the second end portion 16—relative to the overall length of the elongate shaft 10—may vary. For instance, in one embodiment the second end portion 16 is any portion along the length of the elongate shaft 10 extending distally from or otherwise distal to the first end portion 14. In other words, the second end portion 16 may comprise a majority or supermajority of the length of the elongate shaft 10, in comparison to the overall length of the elongate shaft 10 as described above. In yet another embodiment, the second end portion 16 may be less than the majority of the length of the elongate shaft 10, and may be less than 100 cm of the total overall length of the elongate shaft 10. In still another embodiment, the second end portion 16 is from about 0.5 cm to about 50 cm. In yet another embodiment, the second end portion 16 is from about 1 cm to about 25 cm.

The elongate shaft 10 and its second end portion 16 according to the embodiments of FIGS. 1, 1A, 2, 2A, 2B and the other figures is well tolerated by patients and is sized to be suitable for navigating vessel passageways, catheters, endoscope channels, and accessory channels. Moreover, the elongate shaft 10 according to the invention provides additional functionality compared to the conventional wire guide. As discussed more fully below, the flexible second end portion 16 has textures 26, 28, 160, 161 comprising protuberances 26 and/or indentations 28 (FIGS. 1, 1A, 2, and 2A) and/or peaks 160 and valleys 161 (FIGS. 3A, 3B, 4A, 4B, 5, 6, 7, and 8) as taught herein for providing increased outer surface areas for enhancing hydrophilic properties and delivering therapeutic agents.

The elongate shaft flexible second end portion 16 comprises a non-coiled portion 24. The non-coiled portion 24 has advantages over a conventional coiled wire guide, which has a coil wrapped around a wire core made of stainless steel or nitinol. Thus, the coil adds another component to the wire core, whereas the non-coiled portion of the present invention need not add another component, and therefore coiled wire guides increase manufacturing costs compared to a non-coiled portion of the second end portion 16. Also, the purpose of the coil is not to increase surface area as is the non-coiled portion 24 of the present invention. Instead, the coil makes the wire stiff in the transverse direction, whereas the non-coiled portion 24 of the second end portion 16 offers less resistance to bending compared to the same portion having a coil wrapped around it. In addition, the coil has turns that are not circumferential; instead, the turns are longitudinal spaced along the length of the wire core. Furthermore, the coil has turns that stretch apart as the coil bends transversely, which is not encountered with a non-coiled portion 24 of the second end portion 16. When a coil comprises a Teflon coating (which is hydrophobic; not hydrophilic) or a coating of hydrophilic material or a therapeutic agent, then the coating may chip away when the coil's turns separate during stretching. Also, the coating is limited to a coiled structure, whereas the present invention may have other configurations for increasing surface area as described below. Additionally, the coil increases the diameter of the wire guide such that the wire core of stainless steel or nitinol needs to be smaller, whereas the non-coiled portion 24 of the present invention can have a bigger core without being too rigid. By comparison to conventional non-coiled wire guides, the non-coiled portion 24 of the present invention has textures 26, 28, 160, 161 resulting in an increased surface area to provide the wire guide with additional functionality, such as enhancing hydrophilic properties and/or delivering therapeutic agents.

The non-coiled portion 24 defines a longitudinal axis 18. As used herein and throughout to describe embodiments of the invention, the term "longitudinal axis" should be considered to be the approximate lengthwise axis of the second end portion 16, which may be straight or may at times even be curved because the second end portion 16 is flexible. At a given cross section (e.g., along line 1A-1A), the non-coiled portion 24 of the flexible second end portion 16 has a nominal outer circumference 22 disposed substantially uniformly about the longitudinal axis 18 (e.g., the nominal outer circumference 22 defines a substantially uniform radius 19 from the longitudinal axis 18, albeit the radius 19 may change longitudinally as the second end portion 16 tapers distally but at the given cross section the radius 19 is substantially uniform and resulting in a uniform, circular outer surface 12). At the given cross section, the non-coiled portion 24 of the flexible second end portion 16 further comprises an effective perimeter 21 (FIG. 1A) that, owing to textures that are protuberances 26 and/or indentations 28 as discussed below, is a non-circular cross section having a circumferentially undulating configuration (e.g., an undulating effective perimeter 21 and/or outer surface 20) comprising a variable radius 19' as measured from the longitudinal axis 18. The effective perimeter 21 measures greater than the nominal outer circumference 22. For example, if the nominal outer circumference 22 measured $2\pi r$, then the effective perimeter 21 would be greater than $2\pi r$. Furthermore, given irregular surfaces on a microscopic level it should be noted that the nominal outer circumference 22 may be defined as the approximate actual, virtual, or mean circumference of a conventional wire guide had there been no protuberances 26 and no indentations 28, which said textures are explained next.

A plurality of textures such as protuberances 26 and/or indentations 28 are disposed substantially circumferentially about the non-coiled portion nominal outer circumference 22 and radially relative to the longitudinal axis 18. The term "textures," in describing embodiments of the invention, includes an embodiment having only protuberances 26, having only indentations 28, or having both protuberances and indentations 26, 28, respectively, and/or as having only peaks 160 and valleys 161 as described below (FIGS. 3A, 3B, 4A, 4B, 5, 6, 7, and 8) or any combination of protuberances 26, indentations 28, peaks 160, and valleys 161. The term "plurality," as used to describe any of the embodiments discussed herein, means "two or more." Thus, there may be one or more protuberances 26 that thrust radially outward from the nominal outer circumference 22 as in, for example, a mass, and/or one or more indentations 28 that recess radially inward from the nominal outer circumference 22 as in, for example, a depression or dent or negative, or a combination of protuberances 26 and indentations 28. In one embodiment, there are at least three of one or more textures 26, 27, 160, 161 at a given cross section (e.g., along lines 1A-1A, 2A-2A, 2B-2B, 6-6, 7-7, and 8-8) of the flexible second end portion 16.

The non-coiled portion 24 further comprises a first outer surface 12 comprising the nominal outer circumference 22 and defining a first surface area 30. The non-coiled portion 24 further comprises a second outer surface 20 comprising the effective perimeter 21 and defining a second surface area 40 (e.g., a non-circular cross section and undulating circumferential outer surface). The second surface area 40 is greater than the first surface area 30. In other words, the plurality of protuberances 26 and/or indentations 28 disposed circumferentially about the nominal outer circumference 22 of the non-coiled portion 24 of the second end portion 16 will increase the overall surface area of the outer surface 20 such that—all other things being equal at a cross section of the flexible second end portion 16—the surface area 40 having an undulating circumferential outer surface resulting from a plurality of protuberances 26 and/or indentations 28 is greater than the surface area 30 having no protuberances 26 and/or indentations 28.

The protuberances 26 and/or indentations 28 may be any configuration (rounded, oblong, circular, elliptical, rectangular, square, rod-like, polygonal, irregular, etc.) or combination thereof to give the effective perimeter 21 a circumferentially undulating configuration. Not to be confused with a wire guide simply having an elliptical or rectangular cross section, the protuberance 26 includes a structure that emerges outwardly from the nominal outer circumference 22 and comprises the undulating effective perimeter 21 resulting in an undulating circumferential outer surface. Examples of a protuberance 26 include but are not limited to any protuberance, protrusion, bulge, bow, convex, bump, knob, raising, lump, roughed-up or coarse surface or combination thereof. Also, protuberances 26 may thrust radially outward from (or relative to) the nominal outer circumference 22 within any suitable diameter sized consistent with the intended vessel passageway. In one embodiment, the protuberance 26 thrusts radially outward from about 0.001 inches to about 0.020 inches, and in another embodiment from about 0.005 inches to about 0.010 inches. If there is a core body extending through the center of the flexible second end portion 16, then in order for the flexible second end portion 16 to be sized for its intended purpose within a vessel passageway the height of the protuberance 26 may be compensated by a reduction in the nominal diameter of the flexible second end portion 16 and core body diameter.

Likewise and not to be confused with a wire guide simply having an elliptical or rectangular cross section, the indentations 28 include a configuration that emerges inwardly from the nominal outer circumference 22 and comprises the undulating effective perimeter 21 resulting in an undulating circumferential outer surface. Examples of indentations 28 include but are not limited to any indentation, depression, recess, dent, concave, sunken part, impression, pockmark, dimple, pit, impression, cavity, crater, negative, roughed-up or coarse surface or combination thereof. Also, the indentation 28 may thrust radially inward from (or relative to) the nominal outer circumference 22 within any tolerance of the material used for the non-coiled portion 24 and/or within tolerance of the core body diameter so as not to affect mechanical integrity. In one embodiment, the indentation 28 thrusts radially inward from about 0.001 inches to about 0.020 inches, and in another embodiment from about 0.005 inches to about 0.010 inches.

Protuberances 26 may form a ringed pattern on the second outer surface 20 of the non-coiled portion 24, or alternatively may form a diagonal pattern or a random pattern. Likewise, the indentations 28 may form a ringed pattern on the second outer surface 20 of the non-coiled portion 24, or alternatively may form a diagonal pattern or a random pattern. In one embodiment, the non-coiled portion 24 is at least about 5.0 cm in length, and alternatively from about 5.0 cm to about 50.0 cm in length or from about 10.0 cm to about 30.0 cm in length, although the length of the non-coiled portion could be more or less than these ranges as desired. The protuberances 26 and/or indentations 28 may be disposed about 10% to about 90% of the non-coiled portion 24 outer surface, and in another embodiment from about 20% to about 50%. These percentages may be greater or lesser depending on the degree to which one desires to increase the surface area 40 (as defined by the section of the non-coiled portion 24 having protuberances 26 and/or indentations 28 disposed about the nominal outer circumference 22) relative to the surface area 30 (as defined by the non-coiled portion without protuberances 26 and/or indentations 28). Indeed, the protuberances 26 and indentations 28 may be disposed about 1% to 100% of the non-coiled portion 24 as defined by the nominal outer circumference 22. In one embodiment the surface area 40 is at least 20% greater than the surface area 30, while in another embodiment the surface area 40 is at least 50% greater than the surface area 30.

The protuberances 26 and indentations 28 optionally are integrally formed from the second end portion 16. By way of example, the protuberances 26 and indentations 28 may be formed from, molded from, stamped from, or machined or tooled from the material forming the second end portion 16 of the elongate shaft 10. Also, the protuberances 26 could be attached to the second end portion 16. Furthermore, the indentations 28 may be etched, notched, drilled and the like into the second end portion 16. The plurality of protuberances 26 and indentations 28 may be disposed spaced apart over the outer surface 20, may be at overlapping positions and run together, or a combination thereof.

Figure 2:
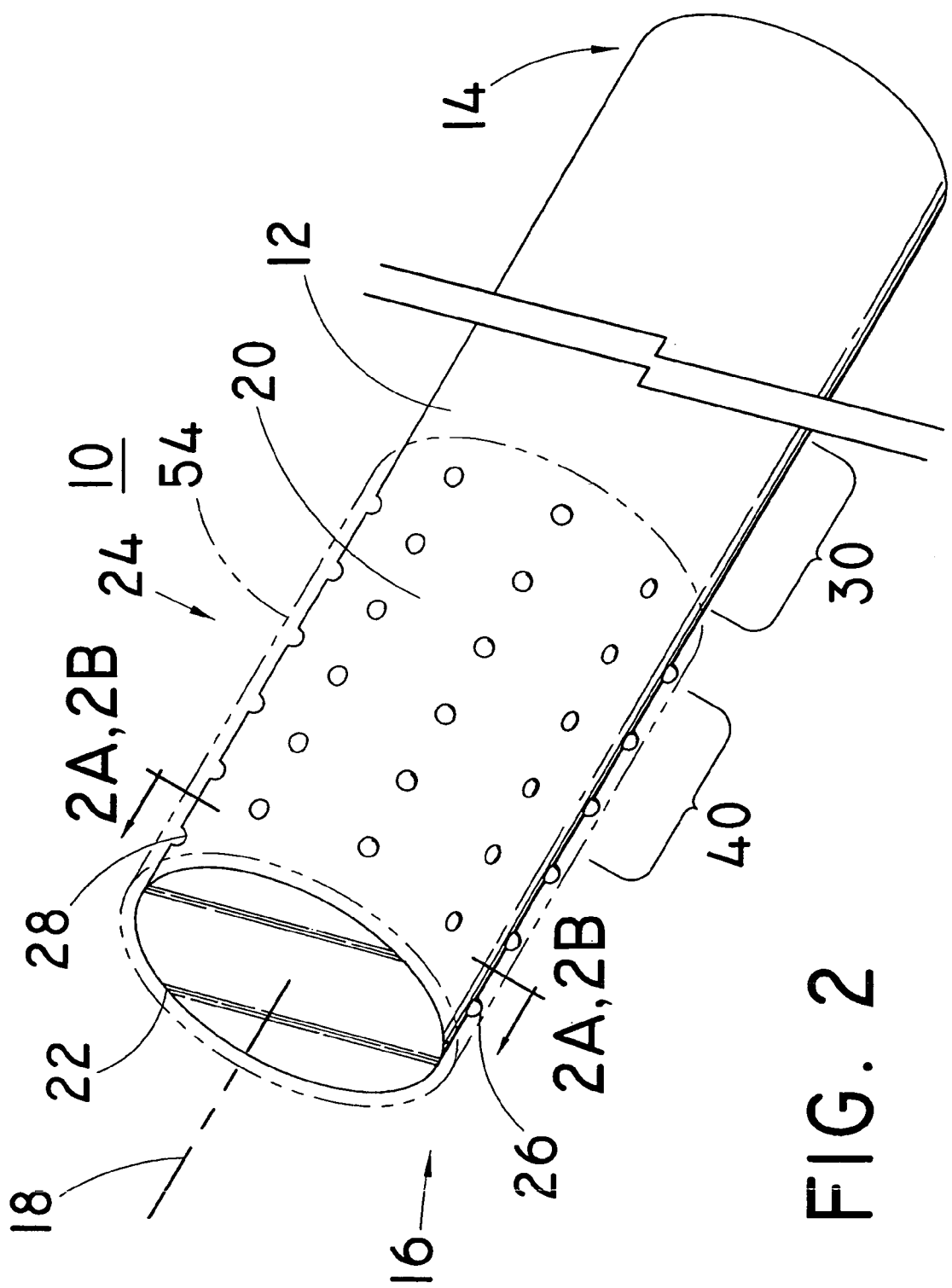
FIG. 2 is a perspective side view, broken away, of a wire guide device according to one embodiment of the invention having a coat.

As shown in FIG. 2 and FIGS. 2A and 2B (the cross section of the flexible second end portion 16 taken along the lines 2A-2A and 2B-2B, respectively, of FIG. 2) where like elements from previous drawings are labeled the same and described above, in one embodiment of the invention, the non-coiled portion 24 of the flexible second end portion 16 further comprises a coating 54 disposed about the non-coiled portion 24 that includes the plurality of protuberances 26 and indentations 28, the coating 54 optionally comprising a hydrophilic material and/or a therapeutic agent. At the given cross section, the coating 54 of the non-coiled portion 24 of the flexible second end portion 16 further comprises a second effective perimeter 21' that owing to protuberances 26 and/or indentations 28 measures greater than the nominal outer circumference 22. In addition, FIG. 2B shows the coating to have a non-circular cross section with a circumferentially undulating configuration (e.g., an undulating second effective perimeter 21' and/or outer surface) comprising a second variable radius 19" as measured from the longitudinal axis 18.

The term "coat," "coating," "coated," and variants thereof when used to describe any embodiment of the invention includes any substance, compound, molecule, or material (whether comprising a solid, liquid, fluid, gel, gas, or vapor) chemically bonded via covalent bonds, ionic bonds, or intermolecular bonds (such as ion-dipole forces, dipole-dipole forces, London dispersion forces, and/or hydrogen bonding), adhered, or otherwise applied by the method(s) of laminating, taping, dipping, spraying, depositing, vapor deposition, wrapping (thermally fusing together), painting and curing, and the like. The coating 54 may be of a generally uniform thickness or of different and/or varying thicknesses. The coating 54 may fill some of the indentations 28 while not filling other indentations 28, and may cover some protuberances 26 while not covering other protuberances 26, and/or may cover some of the outer surfaces 12, 20 while covering less than all of the outer surfaces 12, 20. Furthermore, the coating 54 may form a uniform outer surface as shown in FIG. 2A, or may form an undulating outer surface as shown in FIG. 2B.

In one embodiment, one or more of the plurality of protuberances 26 and/or the coating 54 may comprise a therapeutic agent. In other embodiments, one or more of the plurality of protuberances 26 and/or the coating 54 may comprise a hydrophilic material coated onto the outer surface 20 of the portion 24 of the flexible second end portion 16. Also, therapeutic agent and/or hydrophilic material may be deposited within at least one of the plurality of indentations 28, on the protuberances 26, or between adjacent protuberances 26 on the outer surface 20. In another embodiment, a deposit of therapeutic agent may be coated onto any region of the outer surface 20 of the portion 24 of the flexible second end portion 16.

As used herein to describe any of the embodiments of the invention shown in any of the figures, the term "therapeutic agent" shall be considered to include—by way of illustration and not by way of limitation—any drug, medication, narcotic, antibiotic, pharmaceutical product, and/or medicinal agent, therapy, or substance. Types of therapeutic agents may be active, such as medicine that is utilized during the medical procedure by, for example, assisting with the healing process, assisting to reduce bacterial count, and otherwise delivering medication. Specific examples of therapeutic agents include neomycin, sulfa drugs, antimicrobials, antibiotics, oxybutynin chloride, lidocaine, ketorolac, ketorolac tromethamine, ibuprofen, ketoprofen, Tylenol, and diclofenac and their equivalents, but these or solely for illustrative purposes and not by way of limitation. In one embodiment the therapeutic agent comprises a hydrophilic material. The therapeutic agent optionally may be composed to be soluble to provide timed or slow release.

In still another embodiment, the coating is a hydrophilic material that includes a hydrogel (i.e., a polymer that typically is covalently bonded to the outer surface and is relatively dry until the physician applies water, at which time the polymer swells with an aqueous solution). A hydrogel commonly is 80-90%, and preferably between about 50-98% water by weight in equilibrium. Mechanically, a hydrogel is capable of supporting a tensile stress of between 40,000-60,000 dynes/ cm$^2$. Chemically, hydrogels tend to remain stable and not degrade in vivo.

FIGS. 3A, 3B, 4A, and 4B show additional embodiments of an elongate shaft 110 comprising a first end portion 114 and a flexible second end portion 116 having a non-coiled portion 124 for enhancing hydrophilic properties and/or delivering therapeutic agents. The elongate shaft 110 comprises any elongate structures (e.g., shaft-like, rounded, oblong, circular, rectangular, square, tube-like, generally cylindrical, or rod-like), lengths, diameters, and materials discussed above. Likewise, the flexible second end portion 116 may comprise lengths, tapering diameters, and configurations discussed above. In one embodiment, the elongated shaft 110 is a wire guide. In another embodiment, a wire guide comprises an elongate shaft 110 having a first end portion 114 and a flexible second end portion 116, as described below.

FIGS. 3A, 3B, 4A, and 4B show a nominal outer circumference 122 (as that term is used herein and throughout to describe embodiments) disposed substantially uniformly about a longitudinal axis 118 (e.g., at a given cross section along the length of a non-coiled portion 124, the nominal outer circumference 122 defines a substantially uniform radius 119 from the longitudinal axis 118, albeit the radius 119 may change longitudinally as the second end portion 116 tapers distally but at the same cross section the radius 119 is substantially uniform and resulting in an undulating circular outer surface 112). At the given cross section, the non-coiled portion 124 of the flexible second end portion 116 further comprises an effective perimeter 121 (FIGS. 3A, 3B, 4A, 4B, 6A-8) that, owing to peaks 160 and valleys 161 as discussed below, is a non-circular cross section having a circumferentially undulating configuration (e.g., an undulating effective perimeter 121 and/or outer surface 120) comprising a variable radius 119' as measured from the longitudinal axis 118. The effective perimeter 121 measures greater than the nominal outer circumference 122.

Figure 3A:
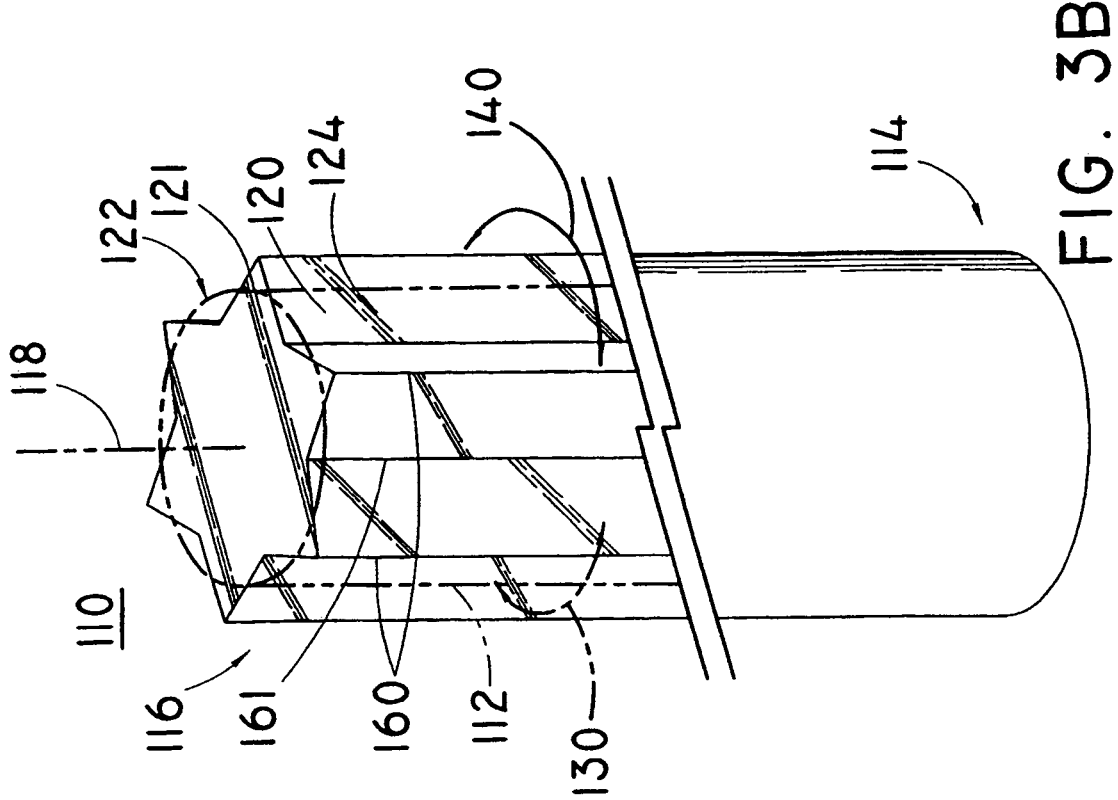
FIGS. 3A and 3B are perspective views, broken away, of wire guide devices according to another embodiment of the invention.
Figure 3B:
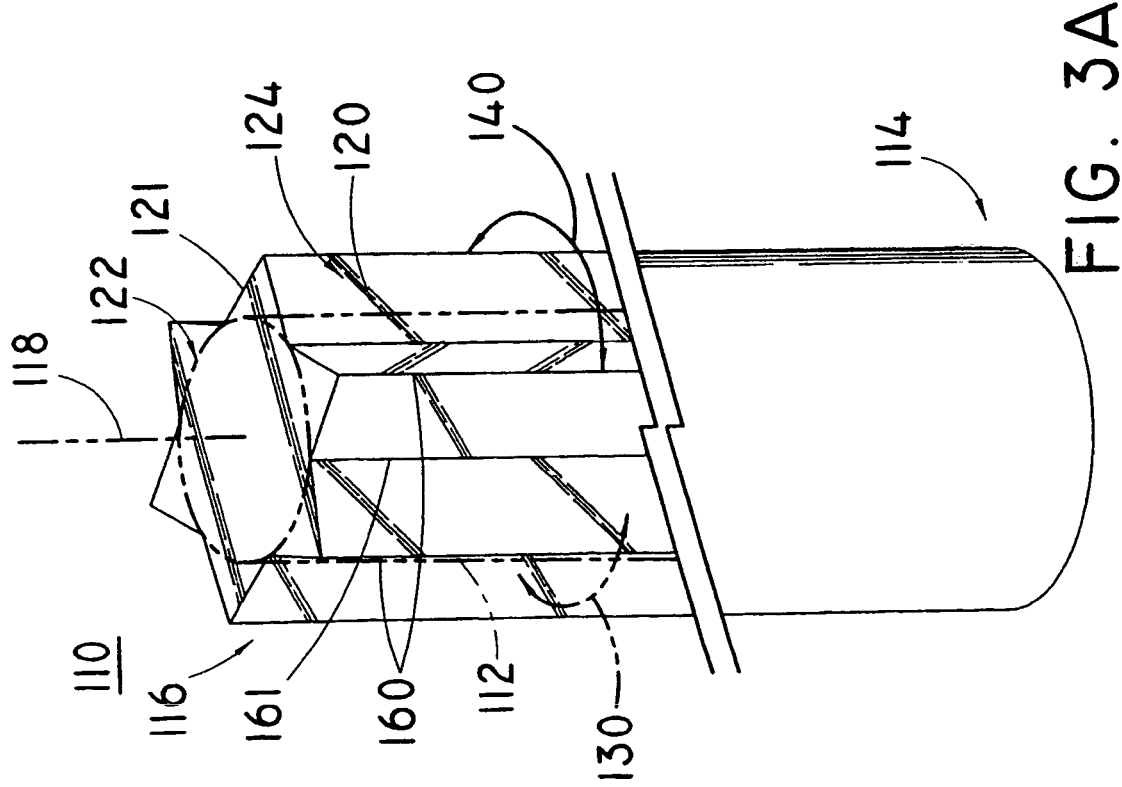

Given irregular surfaces on a microscopic level, the nominal outer circumference 122 (e.g., $2\pi r$) may be defined as the approximate circumference of a conventional wire guide or the mean circumference of a wire guide without the peaks, valleys, or textures taught according to the invention. For example, FIGS. 3A and 4A illustrate the nominal outer circumference 122 of a wire guide as defined by the innermost radial boundary of the peaks and valleys 160, 161, respectively, (or protuberances 26 and indentations 28 in the case of FIGS. 1, 1A, 2, 2A, and 2B). Nevertheless, the nominal outer circumference 122 may be defined as intersecting a radial mid-point of the peaks and valleys 160, 161, respectively, as shown in FIGS. 3B and 4B (or protuberances 26 and indentations 28 as in the case of FIGS. 1, 1A, 2, 2A, and 2B). The nominal outer circumference 122 may also be defined as circumscribing the outermost apices of peaks 160 and valleys 161 or protuberances 26 and indentations 28 (FIGS. 1, 1A, 2, 2A, and 2B).

The flexible second end portion 116 of the elongate shaft 110 embodiments shown in FIGS. 3A, 3B, 4A, and 4B extends distally from or otherwise is distal to the first end portion 114.

The non-coiled portion 124 defines the longitudinal axis 118, which as previously explained, may be straight or curved because the second end portion 116 is flexible. The non-coiled portion 124 further comprises the nominal outer circumference 122 described above, the nominal outer circumference 122 being disposed substantially uniformly about the longitudinal axis 118.

A plurality of peaks 160 and valleys 161 are disposed substantially circumferentially about the non-coiled portion nominal outer circumference 122 and radially relative to the longitudinal axis 118. Adjacent peaks 160 define a valley 161 therebetween. The non-coiled portion 124 further comprises a first outer surface 112 comprising the nominal outer circumference 122 and defining a first surface area 130. Owing to the peaks 160 and valleys 161, the non-coiled portion 124 further comprises a second outer surface 120 comprising an effective perimeter 121 and defining a second surface area 140. Given the non-circular cross section with circumferentially undulating configuration (e.g., an undulating effective perimeter 121 and/or outer surface) as a result of the peaks 160 and valleys 161 disposed substantially circumferentially about the non-coiled portion nominal outer circumference 122, the effective perimeter 121 is greater than the nominal outer circumference 122. For example, if the nominal outer circumference 122 measured 2πr, then the effective perimeter 121 would be greater than 2πr. Consequently, the second surface area 140 is greater than the first surface area 130.

Peaks 160 and valleys 161 may be of any circumferentially undulating configuration that increases the surface area. By way of illustration and not by way of limitation, the peaks 160 and valleys 161 may emerge outwardly from—or inwardly from—the nominal outer circumference 122. Examples include but are not limited to the following shapes formed by the peaks 160 and valleys 161: channeled, corrugated, creased, crescent, curvilinear, D-shaped, finned, folded, furrow, gilled, grooved, indented, pleated, rails, recessed, ribbed, thread, ridged, slitted, slotted, U-shaped, V-shaped, tracks, twisted, waves, helical winding, spiral winding, and/or any combinations thereof along the outer surface. Therefore, it should be noted that the outer surface 120 may comprise an effective perimeter 121 that includes any surface enhancing configuration such as, for example, any apical, pointed, star-shaped, arched, clover-shaped, or other irregular-shaped elongate structure utilized as a wire guide for percutaneous or endoscopic uses.

In one embodiment, at least one of the peaks 160 defines a longitudinal axis offset and substantially parallel to the elongate member longitudinal axis. The peaks 160 may be spaced apart uniformly with respect to adjacent peaks 160 such that the peaks 160 form a ringed pattern (e.g., a shaft having straight, uniformly spaced teeth resembling a gear, toothed wheel, or cylinder, where the teeth are round, square, V-shaped, U-shaped, D-shaped, or other shapes described above in respect to the peaks 160 and valleys 161) on the second outer surface 120. Alternatively, the peaks 160 may be spaced apart irregularly with respect to adjacent peaks 160 such that the peaks 160 form a random pattern on the second outer surface 120. In another embodiment, the peaks 160 may form a diagonal pattern. In one embodiment, the non-coiled portion 124 is a non-coiled flexible second end portion of a wire guide.

Also, a peak 160 may thrust radially outward from (or relative to) the nominal outer circumference 122 within any suitable diameter sized consistent with the intended vessel passageway. In one embodiment, a peak 160 thrusts radially outward from about 0.001 inches to about 0.020 inches, and in another embodiment from about 0.005 inches to about 0.010 inches. If there is a core body extending through the center of the flexible second end portion 116, then in order for the flexible second end portion 116 to be sized for its intended purpose within a vessel passageway the height of the a peak 160 may be compensated by a reduction in the nominal diameter of the flexible second end portion 116 and core body diameter.

Conversely, the valley 161 may thrust radially inward from (or relative to) the nominal outer circumference 122 and, thereby, form the adjacent peaks 160. The valley 161 may thrust radially inward from the nominal outer circumference 122 within any tolerance of the material used for the non-coiled portion 124 and/or within tolerance of the core body diameter so as not to affect mechanical integrity. In one embodiment, the valley 161 thrusts radially outward from about 0.001 inches to about 0.020 inches, and in another embodiment from about 0.005 inches to about 0.010 inches.

In one embodiment, the non-coiled portion 124 is at least about 5.0 cm in length, and alternatively from about 5.0 cm to about 50.0 cm in length or from about 10.0 cm to about 30.0 cm in length, although the length of the non-coiled portion could be more or less than these ranges as desired. Peaks 160 and valleys 161 may be disposed about 10% to about 90% of the non-coiled portion 124 outer surface and in another embodiment from about 20% to about 50%. These percentages may be greater or lesser depending on the degree to which one desires to increase the surface area 140 (as defined by the section of the non-coiled portion 124 having peaks 160 and/or valleys disposed about the nominal outer circumference 122) relative to the surface area 130 (as defined by the non-coiled portion without peaks 160 and/or valleys). Indeed, the peaks 160 and valleys 161 may be disposed about 1% to 100% of the non-coiled portion 124 as defined by the nominal outer circumference 122. In one embodiment the surface area 140 is at least 20% greater than the surface area 130, while in another embodiment the surface area 140 is at least 50% greater than the surface area 130.

The peaks 160 and valleys 161 optionally are integrally formed from the second end portion 116. By way of example, the peaks 160 and valleys 161 may be formed from, molded from, stamped from, or machined or tooled from the material forming the second end portion 116 of the elongate shaft 110. Also, the peaks 160 could be attached to the second end portion 116. Furthermore, the valleys 161 may be etched, notched, drilled and the like into the second end portion 116. The plurality of peaks 160 and valleys 161 may be disposed spaced apart over the outer surface 120, may be at overlapping positions and run together, or a combination thereof.

In one embodiment, a hydrophilic material may be coated onto any of the outer surface 120 of the non-coiled portion 124 of the flexible second end portion 116, as previously described in reference to embodiments of FIGS. 2, 2A, and 2B, such as by depositing the hydrophilic material onto a peak 160 or within a valley 161. In another embodiment, therapeutic agent may be coated onto any of the outer surface 120 of the non-coiled portion 124 of the flexible second end portion 116, and/or over or in at least one of the valleys 161, as previously described. In still another embodiment, one or more of the plurality of peaks 160 may be coated with a therapeutic agent. Therapeutic agents optionally may be composed to be soluble to provide timed or slow release.

Therefore, it should be noted that conventional wire guides, though tapered, have a construction formed generally from any suitable wire guide material with a circular cross section. The elongate shaft 10 with a non-coiled portion 24 comprising protuberances 26 and/or indentations 28 (and the elongate shaft 110 with a non-coiled portion 124 comprising peaks 160 and valleys 161) have non-circular cross sections with undulating effective perimeters and outer surfaces. As a result, the textures 26, 28, 160, 161 increase outer surface area for enhancing hydrophilic properties and delivering therapeutic agents.

FIG. 5 shows a schematic representation of an elongate wire guide 112 according to FIGS. 3A, 3B, 4A, and 4B and include the elements described according to those figures. The peaks 160 and valleys 161 have been removed for simplicity so as to focus on cross sectional embodiments shown in FIGS. 6A-6D, 7, and 8 for enhancing hydrophilic properties and/or delivering a therapeutic agent as previously defined to describe embodiments of the invention. The cross sectional embodiments shown in FIGS. 6A-6D, 7, and 8 are cross sectional views of the non-coiled portion 124 taken along the lines 6-6, 7-7, and 8-8, respectively, of FIG. 5. Reference numerals used to describe FIGS. 6A-6D, 7, and 8 and that are common to FIGS. 3A, 3B, 4A, and 4B have been previously described above, which descriptions are incorporated by reference.

For simplicity, the peaks 160 and valleys 161 in FIGS. 6A-6D, 7, and 8 schematically resemble the peaks 160 and valleys 161 shown in FIGS. 4A and 4B by way of example and not by way of limitation, but should be understood to include peaks 160 and valleys 161 shown in FIGS. 3A and 3B as well as all peaks 160 and valleys 161 consistent with this disclosure. In addition, FIGS. 6A-6D, 7, and 8 show a cross section at a non-coiled portion 124 but do not label many elements that are present but were already discussed in reference to FIGS. 3A, 3B, 4A, and 4B, including but not limited to a substantially uniform radius 119, a variable radius 119', a first surface area 130, and a second surface area 140, as those elements were discussed above.

In FIGS. 6A and 6B, the non-coiled portion may carry therapeutic agents in the valleys 161. Also, the peaks 160 may carry therapeutic agents. Moreover, the wire guide may have a coat 74 (as previously described) that comprises therapeutic agents. FIG. 6A shows the coat 74 of a generally uniform thickness, while FIG. 6B illustrates a coat 74 of different and varying thicknesses.

FIGS. 6C and 6D further show a membrane 84. The term "membrane" as used to describe any embodiment of the invention includes any substance, compound, molecule, or material (whether comprising a solid, liquid, fluid, gel, gas, or vapor) chemically bonded via covalent bonds, ionic bonds, or intermolecular bonds (such as ion-dipole forces, dipole-dipole forces, London dispersion forces, and/or hydrogen bonding), adhered, or otherwise applied by the method(s) of shrink wrapping, laminating, taping, dipping, spraying, depositing, vapor deposition, wrapping (thermally fusing together), painting and curing, and the like. The membrane 84 may be of a generally uniform thickness or of different and/or varying thicknesses. The membrane 84 may comprise a therapeutic agent. In addition, the membrane 84 may be permeable for allowing therapeutic agent in the coat 74, the peaks 160, or in any of the valleys 161 to move through the membrane 84 and to a space exterior the membrane 84.

In FIGS. 6A, 6B, 6C, and 6D, the coat 74 has an inner surface 75. The coat 74 may be configured so that the inner surface 75 is flush against the peaks and valleys 160, 161, respectively, or configured so as to not entirely cover every peak 160 and every valley 161, i.e., the entire outer surface 120. Instead, there may be a space between the inner surface 75 of the coat 74 and the outer surface 120 of the non-coiled portion 124—owing to peaks and valleys 160, 161, respectively, as previously described and/or the non-circular or asymmetrical cross section of the non-coiled portion 124, e.g., rectangular or trapezoidal, D-shaped, triangular, rectangular, polygonal, trapezoidal, hexagonal, pentagonal, and/or any combinations thereof.

FIGS. 7 and 8 show a membrane 84 and at least one reservoir 73, and optionally a plurality of reservoirs 73, for delivering a therapeutic agent 90. As used to describe any embodiment herein, the term "delivering" and variants thereof should be understood to include delivering, carrying, transporting, depositing, depository, repository, supplying, containing, or storing a therapeutic agent as that term has been previously defined to described embodiments of the invention. It should be noted that these reservoirs 73 of FIGS. 7 and 8, or the valleys 161 of FIG. 6A-6D, may comprise any ridge-shaped, V-shaped, U-shaped, L-shaped, crescent-shaped, projection, depression, indentation, or other structure formed in the elongate shaft 110 for delivering a therapeutic agent 90. In another embodiment of FIGS. 7 and 8, the membrane 84 comprises a therapeutic agent.

In FIGS. 7 and 8, a reservoir 73 may extend along a portion of at least one valley 161 along the outer surface 120 of the second end 116 and extend to a space exterior to the to the outer surface 120. It should be noted that a space exterior includes any space outside of the shaft 110, whether that space is transverse to the elongate member longitudinal axis, intermediate the first and second ends 114, 116, respectively, or distally beyond the second end 116.

In one embodiment of a non-coiled portion of an elongate shaft according to FIGS. 7 and 8, the reservoir 73 comprises a therapeutic agent 90. FIGS. 7 and 8 show a plurality of reservoirs filled with a therapeutic agent 90 for delivering the therapeutic agent 90. The reservoirs also may be partially filled with therapeutic agent 90. The therapeutic agent 90 may comprise a gel, a liquid, a soluble deposit, or a foam formed from polyvinyl acetate, polyurethane, silicone, polyester, polyethylene and the like comprising a therapeutic agent 90.

The foam, soluble deposit, gel, liquid, or coat may be a drug eluting therapeutic agent 90 configured to release the drug at a desired rate into the body in order to provide timed and extended drug release. The therapeutic agents may be physically packed into or chemically bonded via covalent bonds, ionic bonds, or intermolecular bonds (such as ion-dipole forces, dipole-dipole forces, London dispersion forces, and/or hydrogen bonding), adhered, or otherwise applied to any portion of the reservoir 73. Other types of therapeutic agents may comprise inactive coatings, such as AQ® hydrophilic. Still other therapeutic agents may comprise biodegradable polymers that are active, inactive, or polymeric. Moreover, the membrane 84 may be any coating, layer, film, spray-on, substrate, bathing solution, deposit, plotting, or shrink wrap of material (e.g., polymer) that is applied to and/or covers, cloaks, blankets, surrounds, spots, or encapsulates partially or more any portion of the outer surface 120 of the second end 116.

Another embodiment includes a reservoir 73 wherein the therapeutic agent is deposited in one or more of the valleys 161. By way of example, one embodiment includes a reservoir 73 positioned between the outer surface 120 and the membrane 84 surrounding at least a portion of the outer surface 120 along a portion of the second end 116. As used herein and above to describe any embodiments according to the invention, the portion may be but need not surround the entire nominal outer circumference 122, the perimeter 121, and/or the outer surface 120, and surround should be understood as including less than all of the nominal outer circumference 122, the perimeter 121, and/or the outer surface 120 or may be any blotch along the outer surface 120.

For example, owing to the peaks and valleys 160, 161, respectively, a membrane 84 may be configured so as to not entirely cover every peak 160 and every valley 161, i.e., the entire outer surface 120. Instead, the membrane 84 leaves a space (passageway) between an inner surface 85 of the membrane 84 and the outer surface 120, owing to peaks and valleys 160, 161, respectively, as previously described and/or the non-circular or asymmetrical cross section of the non-coiled portion, e.g., rectangular or trapezoidal, D-shaped, triangular, rectangular, polygonal, trapezoidal, hexagonal, pentagonal, and/or any combinations thereof.

In another embodiment, the membrane 84 is partially shrink wrapped such that, owing to the peaks and valleys 160, 161, respectively, at least one lumen 76 is formed in at least one of the valleys 161 between the outer surface of the valley 161 and an inner surface 85 of the membrane 84. Optionally, the lumen 76 has a distal port 77, which should be understood to include any port, opening, and the like, extending to a space exterior to the elongate member outer surface area 120, whereby the lumen 76 carries the therapeutic agent to the distal port 77.

It should be noted that the embodiment of the elongate shafts 10 and 110 of FIGS. 1, 1A, 2, 2A, 2B, 3A, 3B, 4A, and 4B may be combined with or used as the elongate shaft 110 of FIGS. 5, 6A, 6B, 6C, 6D, 7, and 8. For instance, the elongate shaft 10 of the medical device may comprise a plurality of peaks 160 and valleys 161, as previously described and disclosed in FIGS. 3 and 4, along the outer surface 20 of the elongate shaft 10, whereby adjacent peaks 160 define a valley 161 therebetween. As a further example, the elongate wire guide 110 optionally may comprise a plurality of peaks and valleys 160, 161, respectively, as well as protuberances 26 and indentations 28 discussed above and shown in FIGS. 1, 1A, 2, 2A, and 2B.

Also, the present inventions described herein above do not foreclose an elongate shaft 10 comprising a coil and, indeed, the second end 16 may include a coil. In other words, the present inventions comprise a portion 24 (FIGS. 1, 1A, 2, and 2A), 124 (FIGS. 3A, 3B, 4A, 4B, 5-8) that does not have a coil. The term "comprise" means that the wire guide device may also include a coiled structure so long as the wire guide device includes a non-coiled portion 24, 124 according to the invention.

Methods

Conventional methods of providing a wire guide device for intracorporeal procedures utilize wire guides having generally smooth outer guide wire surfaces. The present invention comprises methods of providing a wire guide having novel outer surface areas and reservoirs for enhancing hydrophilic properties and delivering therapeutic agents.

Figure 9:
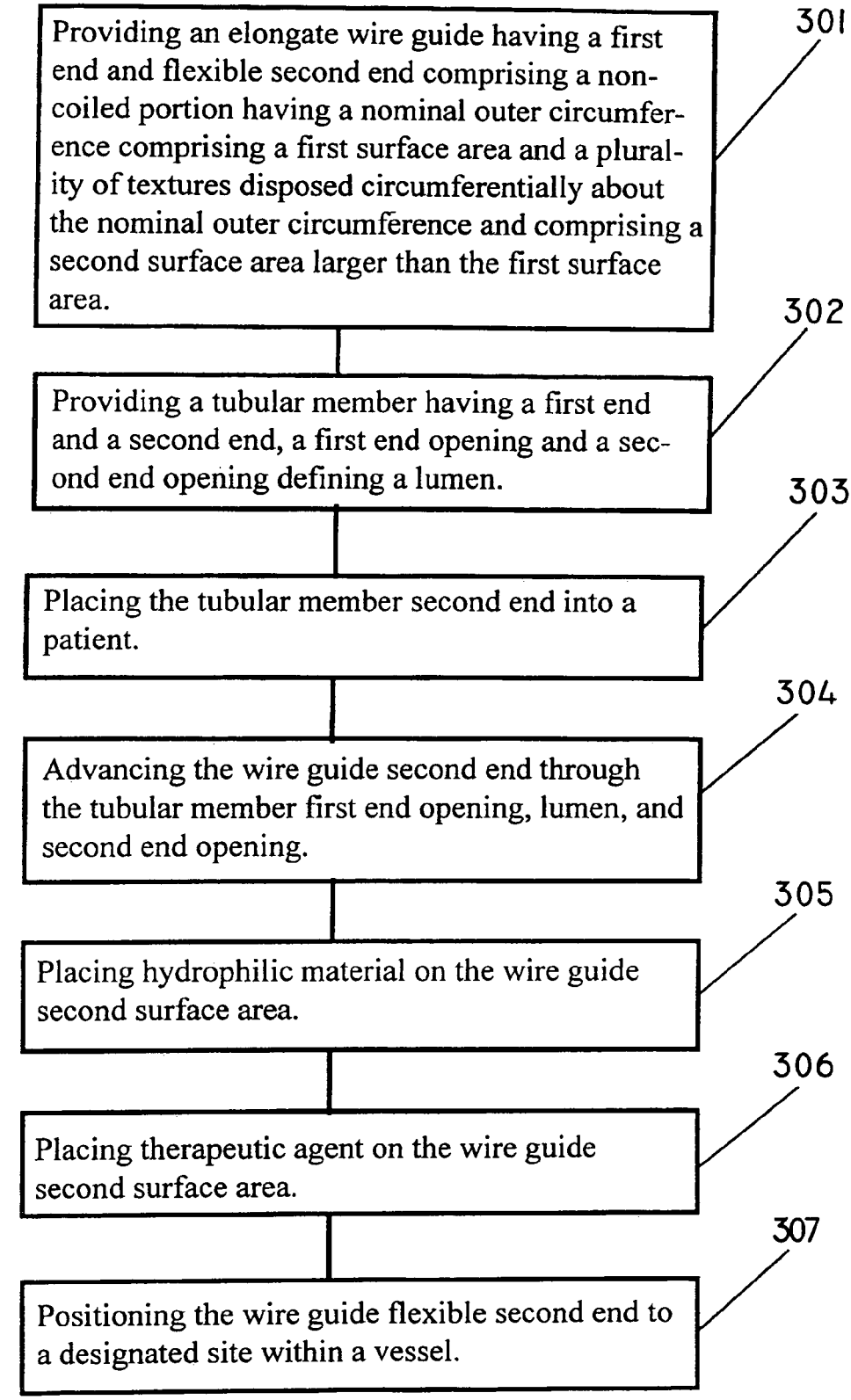
FIG. 9 is a block diagram illustrating a method of the invention.

FIG. 9 shows one embodiment of the method 300 according to the invention. An elongate wire guide 10, 110 having a first end 14, 114 and flexible second end 16, 116 comprising a non-coiled portion 24, 124 having a nominal outer circumference 22, 122 comprising a first surface area 30, 130 and a plurality of surface area enhancers 26, 28, 160, 161 disposed circumferentially about the nominal outer circumference 22, 122 and comprising a second surface area 40, 140 larger than the first surface area 30, 130 is provided (step 301).

More particularly, an elongate wire guide 10 is provided (step 301) with a first end 14 and a flexible second end 16 having a portion 24 comprising a nominal outer circumference 22 and a first outer surface 12 comprising the nominal outer circumference 22 and defining a first surface area 30. One or more or a combination of one or more textures comprising protuberances 26 and/or indentations 28 (individually or in any combination) are disposed circumferentially about the nominal outer circumference 22 and define an effective perimeter 21 greater than the nominal outer circumference 22 and having a second outer surface 20 comprising the effective perimeter 21 and defining a second surface area 40. The second surface area 40 is greater than the first surface area 30 as described above in reference to embodiments of devices according to the invention.

In another embodiment, an elongate wire guide 110 is provided (step 301) with a first end 114 and a flexible second end 116 having a portion 124 comprising a nominal outer circumference 122 and a first outer surface 112 comprising the nominal outer circumference 122 and defining a first surface area 130. One or more or a combination of one or more textures comprising peaks 160 and valleys 161 are disposed circumferentially about the nominal outer circumference 122 and define an effective perimeter 121 greater than the nominal outer circumference 122 and having a second outer surface 120 comprising the effective perimeter 121 and defining a second surface area 140. The second surface area 140 is greater than the first surface area 130 as described above in reference to embodiments of devices according to the invention.

A tubular member is provided (step 302). The tubular member may be a cannula, a needle, an endoscope working channel, or an accessory channel used with an endoscope having openings at first and second ends and defining a lumen therebetween for endoscopic or percutaneous use. The tubular member second end is placed (step 303) into a patient endoscopically or percutaneously. However, it should be understood that more than the second end may be placed into the patient, an internal region of the patient's body, or the epidermis of the patient. The wire guide second end is advanced (step 304) (e.g., inserted) into the tubular member first end opening, through the tubular member lumen, and external to the second end opening, where the wire guide second end is disposed in the first vessel passageway of a patient and is positioned at a target site.

The method 300 may further comprise placing (step 305) hydrophilic material on the wire guide second surface area 40, 140. The method may further comprise placing (step 306) therapeutic agent on the wire guide second surface area 40, 140. The method may further comprise positioning (step 307) the wire guide flexible second end 16, 116 to a designated site within a vessel. The method may further comprise the tubular member comprising an endoscope wherein the second end is a flexible distal insertion portion with a distal light and lens for visualizing the interior of an internal region of a body and the lumen is a working channel for passing said wire guide.

The method 300 need not be performed sequentially. For instance, therapeutic agent may be placed (step 305) before the tubular member is provided (step 302) or placed (step 303) into a patient, or before the wire guide is advanced (step 304) through the tubular member. Likewise, hydrophilic material may be placed (step 305) before the tubular member is provided (step 302) or placed (step 303) into a patient, or before the wire guide is advanced (step 304) through the tubular member.

It is intended that the foregoing detailed description of the medical devices and methods be regarded as illustrative rather than limiting, and that it be understood that it is the following claims, including all equivalents, that are intended to define the spirit and scope of this invention. Terms are to be given their reasonable plain and ordinary meaning. Also, the embodiment of any figure and features thereof may be combined with the embodiments depicted in other figures. Other features known in the art and not inconsistent with the structure and function of the present invention may be added to the embodiments.

While particular elements, embodiments and applications of the present invention have been shown and described, it will be understood, of course, that the invention is not limited thereto since modifications may be made by those skilled in the art, particularly in light of the foregoing teachings. Therefore, it is therefore contemplated by the appended claims to cover such modifications as incorporate those features which come within the spirit and scope of the invention.

What is claimed is:

1. A wire guide device for use within a gastrointestinal track comprising:

A wire guide comprising an elongate shaft having a longitudinal axis, a first end portion, and a flexible second distal end portion, the distal second end portion comprising a non-coiled portion, the non-coiled portion comprising a wire guide core and further comprising a first outer surface and a first surface area, the elongate shaft tapering in a distal direction such that a first end portion diameter is greater than a second end portion diameter;

a plurality of textures being integrally formed from the wire guide second end portion, the textures being disposed substantially circumferentially about the non-coiled portion of the distal second end portion, at least one of the textures emerging radially outwardly and at least one of the textures emerging radially inwardly such that the textures form peaks and valleys at a cross section of the non-coiled portion such that the cross section comprises a circumferentially undulating effective perimeter about the longitudinal axis, wherein the non-coiled portion with the textures comprises a second outer surface having a second surface area that is greater than the first surface area without textures and further comprising a substantially uniform column strength and flexibility; and a permeable member attached to adjacent peaks such that it forms at least one or more reservoir extending longitudinally in the distal direction of the longitudinal axis between the outwardly radiating adjacent peaks along the second outer surface of the second end portion, the reservoir being configured to allow delivery of at least one of a therapeutic agent and hydrophilic material through the permeable membrane;

wherein the membrane is partially shrink wrapped about adjacent peaks such that the reservoir is formed in the valley therebetween the adjacent peaks, the reservoir having a distal port extending to a space exterior to the elongate wire guide second end.

2. The device of claim 1 wherein at least one texture thrusts radially outward from about 0.001 inches to about 0.020 inches relative to the nominal outer circumference.

3. The device of claim 1 wherein at least one texture thrusts radially inward from about 0.001 inches to about 0.020 inches relative to the nominal outer circumference.

4. The device of claim 1 wherein the non-coiled portion is at least about 5.0 cm in length.

5. The device of claim 1 wherein the textures are disposed about 10% to about 90% of the non-coiled portion.

6. The device of claim 1 wherein at least one texture comprises an indentation.

7. The device of claim 1 wherein the peaks are integrally formed from the wire guide second end portion such that adjacent peaks define the valley therebetween.

8. The device of claim 7 wherein adjacent peaks defining the valley form a shape selected from the group consisting of channeled, corrugated, creased, crescent, curvilinear, D-shaped, finned, folded, furrow, gilled, grooved, indented, pleated, rails, recessed, ribbed, threaded, ridged, slitted, slotted, U-shaped, V-shaped, tracks, twisted, waves, helical winding, spiral winding, and any combinations thereof.

9. The device of claim 7 further comprising a hydrophilic agent deposited in at least one valley.

10. The device of claim 7 further comprising a therapeutic agent deposited in at least one valley.

11. The device of claim 1 further comprising a coating disposed at least partially about the shrink wrapped membrane.

12. The device of claim 11 wherein the coating comprises at least one of a hydrophilic material and a therapeutic agent.

13. The device of claim 1 wherein at least one of the plurality of textures further comprises therapeutic agent.

14. The device of claim 1 wherein at least one of the plurality of textures further comprises hydrophilic material.

15. The device of claim 1 wherein the reservoir is substantially parallel to the elongate shaft longitudinal axis along the distal second end portion.

16. The device of claim 1 wherein the reservoir is substantially diagonal to the elongate shaft longitudinal axis along the distal second end portion.

17. The device of claim 1 wherein the reservoir formed between adjacent textures comprises a shape selected from the group consisting of corrugated, creased, crescent, curvilinear, D-shaped, finned, folded, furrow, gilled, grooved, indented, pleated, rails, recessed, ribbed, threaded, ridged, slitted, slotted, U-shaped, V-shaped, tracks, twisted, waves, helical winding, and spiral winding.

* * * * *

UNITED STATES PATENT AND TRADEMARK OFFICE
CERTIFICATE OF CORRECTION

PATENT NO. : 7,637,873 B2  Page 1 of 1
APPLICATION NO. : 11/377712
DATED : December 29, 2009
INVENTOR(S) : Kenneth C. Kennedy, II It is certified that error appears in the above-identified patent and that said Letters Patent is hereby corrected as shown below:

In the Claims

In column 16, claim 1, line 64, before "comprising:" replace "track" with --tract--.

In column 16, claim 1, line 65, before "wire guide" replace "A" with --a--.

In column 17, claim 1, line 21, after "flexibility; and a permeable" replace "member" with --membrane--.

Signed and Sealed this

Sixth Day of April, 2010

David J. Kappos
*Director of the United States Patent and Trademark Office*